United States Patent
Eidenschink

(10) Patent No.: US 8,636,707 B2
(45) Date of Patent: *Jan. 28, 2014

(54) BIFURCATED STENT DELIVERY SYSTEM

(75) Inventor: Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 316 days.

This patent is subject to a terminal disclaimer.

(21) Appl. No.: 12/562,016

(22) Filed: Sep. 17, 2009

(65) Prior Publication Data

US 2010/0004594 A1    Jan. 7, 2010

Related U.S. Application Data

(63) Continuation of application No. 10/631,444, filed on Jul. 30, 2003, now Pat. No. 7,604,621.

(51) Int. Cl.
*A61M 25/00* (2006.01)

(52) U.S. Cl.
USPC ..................... 604/284; 604/101.04

(58) Field of Classification Search
USPC ................ 604/284, 101.01, 101.04, 96.01, 604/103.05, 171, 530, 43
See application file for complete search history.

(56) References Cited

U.S. PATENT DOCUMENTS

| | | | |
|---|---|---|---|
| 4,994,071 A | 2/1991 | MacGregor | |
| 5,613,949 A * | 3/1997 | Miraki | 604/101.01 |
| 5,613,980 A | 3/1997 | Chauhan | |
| 5,669,924 A | 9/1997 | Shaknovich | |
| 5,681,345 A | 10/1997 | Euteneuer | |
| 5,718,724 A | 2/1998 | Goicoechea et al. | |
| 5,720,735 A | 2/1998 | Dorros | |
| 5,723,004 A | 3/1998 | Dereume et al. | |
| 5,749,825 A | 5/1998 | Fischell et al. | |
| 5,755,735 A | 5/1998 | Richter et al. | |
| 5,788,707 A | 8/1998 | Del Toro et al. | |
| 6,066,155 A | 5/2000 | Amann et al. | |
| 6,066,166 A | 5/2000 | Bischoff et al. | |
| 6,096,045 A | 8/2000 | Del Toro et al. | |
| 6,099,497 A * | 8/2000 | Adams et al. | 604/96.01 |
| 6,129,738 A | 10/2000 | Lashinski et al. | |
| 6,159,187 A | 12/2000 | Park et al. | |
| 6,221,097 B1 | 4/2001 | Wang et al. | |
| 6,331,186 B1 | 12/2001 | Wang et al. | |
| 6,342,066 B1 | 1/2002 | Toro et al. | |
| 6,350,277 B1 | 2/2002 | Kocur | |
| 6,436,090 B1 | 8/2002 | Sanchez et al. | |
| 6,443,880 B2 | 9/2002 | Blais et al. | |
| 6,475,208 B2 | 11/2002 | Mauch | |

(Continued)

FOREIGN PATENT DOCUMENTS

| | | |
|---|---|---|
| GB | 2385530 | 8/2003 |
| JP | 8-215312 A | 8/1996 |

(Continued)

*Primary Examiner* — Laura Bouchelle

(74) *Attorney, Agent, or Firm* — Seager, Tufte & Wickhem, LLC

(57) ABSTRACT

Systems for treating a vessel bifurcation comprise a bifurcated catheter having a first branch and a second branch. Each branch defining an exchange region that extends from the distal end of the shaft to the guidewire port of the shaft. The catheter has a radial alignment mechanism which provides improved radial alignment characteristics of at least the exchange region of the branches.

8 Claims, 8 Drawing Sheets

(56) References Cited

U.S. PATENT DOCUMENTS

| | | |
|---|---|---|
| 6,478,814 B2 | 11/2002 | Wang et al. |
| 6,482,211 B1 | 11/2002 | Choi |
| 6,494,875 B1 | 12/2002 | Mauch |
| 6,508,836 B2 | 1/2003 | Wilson et al. |
| 6,579,312 B2 | 6/2003 | Wilson et al. |
| 6,582,394 B1 | 6/2003 | Reiss et al. |
| 6,599,315 B2 | 7/2003 | Wilson |
| 6,692,483 B2 | 2/2004 | Vardi et al. |
| 6,746,411 B2 | 6/2004 | Khaw |
| 6,770,092 B2 | 8/2004 | Richter |
| 6,780,174 B2 | 8/2004 | Mauch |
| 6,905,477 B2 | 6/2005 | McDonnell et al. |
| 6,939,368 B2 | 9/2005 | Simso |
| 7,105,019 B2 | 9/2006 | Hojeibane |
| 7,238,197 B2 | 7/2007 | Sequin et al. |
| 7,276,043 B2 * | 10/2007 | Heath et al. ............ 604/6.16 |
| 7,393,339 B2 | 7/2008 | Zawacki et al. |
| 7,604,621 B2 * | 10/2009 | Eidenschink ............ 604/284 |
| 2001/0012927 A1 | 8/2001 | Mauch |
| 2001/0056297 A1 | 12/2001 | Hojeibane |
| 2002/0082548 A1 | 6/2002 | Sanchez et al. |
| 2003/0028233 A1 | 2/2003 | Vardi et al. |
| 2003/0074047 A1 | 4/2003 | Richter |
| 2003/0093109 A1 | 5/2003 | Mauch |
| 2003/0097169 A1 | 5/2003 | Brucker et al. |
| 2003/0114912 A1 | 6/2003 | Sequin et al. |
| 2003/0125802 A1 | 7/2003 | Callol et al. |
| 2003/0135259 A1 | 7/2003 | Simso |
| 2003/0144623 A1 | 7/2003 | Heath et al. |
| 2003/0149444 A1 | 8/2003 | Khaw |
| 2004/0167463 A1 * | 8/2004 | Zawacki et al. ............ 604/43 |

FOREIGN PATENT DOCUMENTS

| | | |
|---|---|---|
| JP | 11-57019 A | 3/1999 |
| JP | 2002-360701 A | 12/2002 |
| WO | 9636269 | 11/1996 |
| WO | 9915103 | 4/1999 |
| WO | 0044307 | 8/2000 |
| WO | 02091951 | 11/2002 |
| WO | 03/053507 A1 | 7/2003 |

* cited by examiner

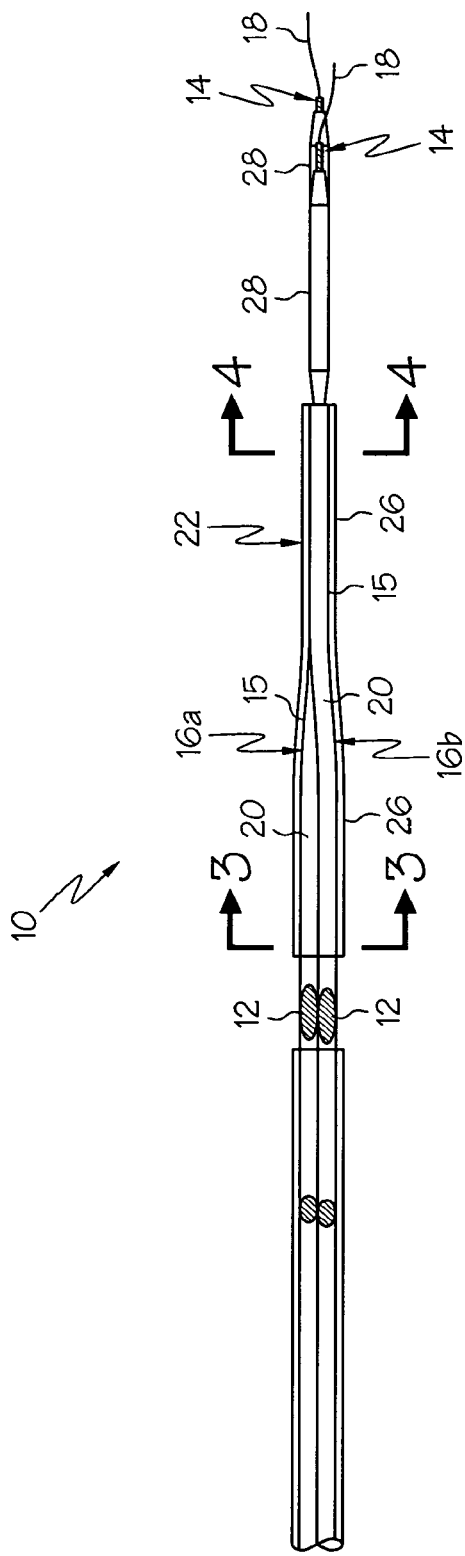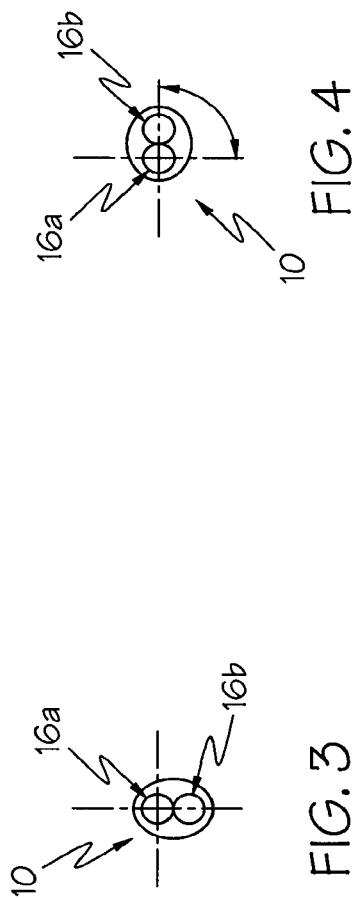

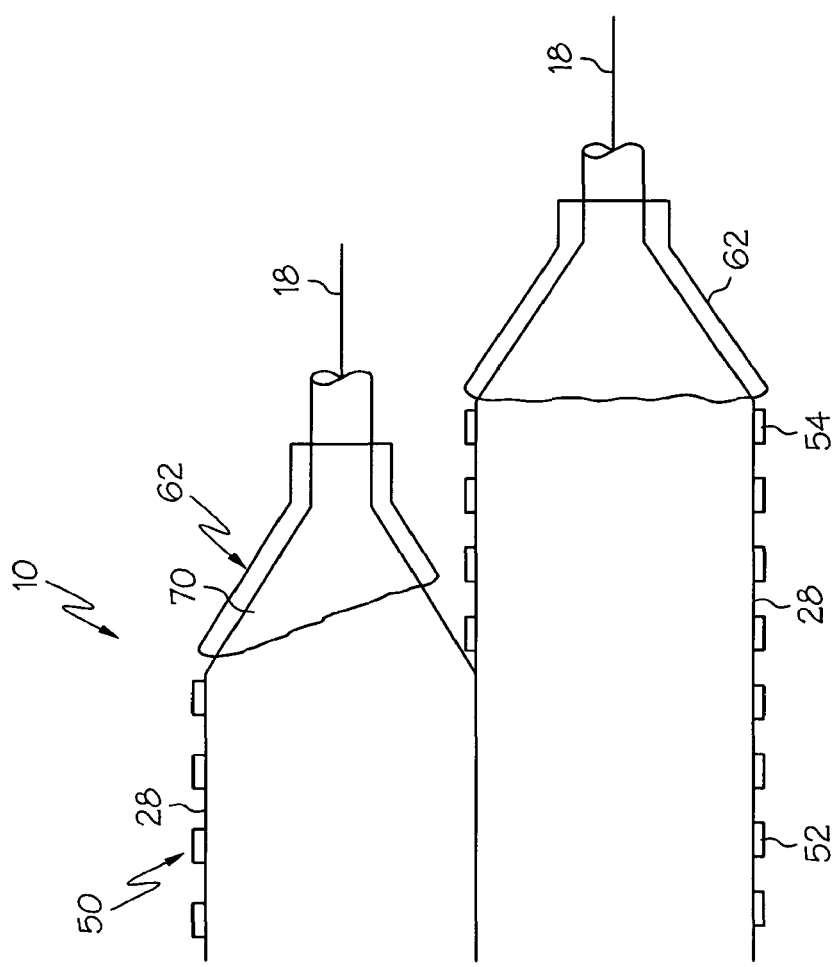

BIFURCATED STENT DELIVERY SYSTEM

CROSS-REFERENCE TO RELATED APPLICATIONS

This application is a continuation of U.S. patent application Ser. No. 10/631,444, now U.S. Pat. No. 7,604,621, filed Jul. 30, 2003, entitled "BIFURCATED STENT DELIVERY SYSTEM", which is hereby incorporated by reference.

STATEMENT REGARDING FEDERALLY SPONSORED RESEARCH

Not Applicable

BACKGROUND OF THE INVENTION

1. Field of the Invention

This invention relates to catheters and catheter assemblies for use in medical procedures. More specifically, the present invention is directed to catheter assemblies for use in treating stenoses at one or more vessel bifurcations.

2. Description of the Related Art

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter which is introduced into and advanced through a lumen or body vessel until the distal end thereof is at a desired location in the vasculature. Once in position across a lesion site, the expandable portion of the catheter, or balloon, is inflated to a predetermined size with a fluid at relatively high pressures, to radially compress the atherosclerotic plaque of the lesion against the inside of the artery wall and thereby dilate the lumen of the artery. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Some stents have been developed specifically to address the problems that arise in the treatment of stenoses at or near the site of a bifurcation of a body lumen are known in the art. Further, single bifurcated stents and grafts have been developed in order to treat such conditions at the site of a branch of a body lumen. A bifurcated stent and/or graft typically is configured in a "pant" design which comprises a tubular body or trunk and two tubular legs, however other configurations are also known wherein the stent includes a plurality of separate and/or inter-connectable portions which may be delivered to various positions at or around the bifurcation using a single or multiple catheters. Some examples of bifurcated stents are shown in U.S. Pat. No. 5,723,004; U.S. Pat. No. 4,994,071; and U.S. Pat. No. 5,755,735.

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. No. 5,681,345; U.S. Pat. No. 5,788,707; U.S. Pat. No. 6,066,155; U.S. Pat. No. 6,096,045; U.S. Pat. No. 6,221,097; U.S. Pat. No. 6,331,186; U.S. Pat. No. 6,342,066; U.S. Pat. No. 6,350,277; U.S. Pat. No. 6,443,880; and U.S. Pat. No. 6,478,814.

Various techniques have been used to deliver bifurcated stents in order to provide radial support to both a main blood vessel, and contemporaneously to side branches of the blood vessel. Examples of catheters for use in treating bifurcated lumens or delivery systems for bifurcated stents, are shown in U.S. Pat. No. 5,720,735; U.S. Pat. No. 5,669,924; U.S. Pat. No. 5,749,825; U.S. Pat. No. 5,718,724; and U.S. Pat. No. 6,129,738. As maybe seen from these references, in many bifurcated stent delivery systems, the bifurcated stent is mounted on a catheter assembly which comprises essentially two balloon catheters mounted in a guide catheter assembly.

Providing a bifurcated catheter, and particularly providing the secondary portion of the catheter with proper radial alignment and sufficient flexibility to be readily advanced and positioned into the side branch of the bifurcation is a significant issue with many bifurcated catheter assemblies. Another issue which exists in some bifurcated catheter assemblies for use in delivering a bifurcated pant design stent is that retention systems for retaining the side component of the stent contribute undesirably to the diameter of the catheter and may inadequately retain and/or improperly retract from one or more ends of the stent branches or legs prior to and/or during delivery.

The present invention seeks to address these problems by providing catheter assemblies with a variety of embodiments and features which improve catheter performance and side branch accessibility.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As indicated above the present invention is embodied in a variety of forms. For example, in at least one embodiment the invention is directed to providing a bifurcated catheter with improved radial alignment characteristics. The term "radial alignment" as it is used herein refers to the characteristic of a bifurcated catheter to align the side branch or leg of the catheter with the side branch of the vessel to which the side leg of the catheter is to be positioned within and/or adjacent to. By providing a catheter with improved radial alignment characteristics the ease or readiness of radially aligning the side leg of the catheter with the side branch of the vessel during advancement of the catheter is increased or otherwise improved.

In some embodiments radial alignment of a catheter is improved by providing the distal end portion of the catheter with a shorter exchange length, wherein the length of the distal end portion of either branch of the catheter between the distal tip and the guidewire port is about 10 cm to about 20 cm. In at least one embodiment the exchange length is no more than about 15 cm.

In at least one embodiment the distal end region of a bifurcated catheter is provided with a partially twisted configuration within the distal sheath wherein the side branch of the catheter is at least partially twisted about the main branch. In some embodiments the distal end portion of the side branch of the catheter is provided with about a ¼, or about a 90 degree, displacement or 'twist' about the distal end portion of the main branch of the catheter. In some embodiments the twist is less than ¼ or 90 degrees. In some embodiments the twist is greater than ¼ or 90 degrees.

In at least one embodiment the portion of a bifurcated catheter distal of one or both guidewires ports is unsheathed.

In at least one embodiment, at least a portion of a side branch of a bifurcated catheter is provided with a stiffening segment. In some embodiment the stiffening segment comprises a sheath disposed about a portion of the guidewire lumen of the side branch. In some embodiments the sheath has a spiral or clam-shell configuration. In some embodiments the sheath is constructed of high density polyethylene (HDPE). In some embodiments the sheath comprises one or more segments. In some embodiments the sheath is disposed about the region of the guidewire lumen which underlies the stent mounting region of the catheter branch.

Some embodiments of the invention are also directed to providing a catheter with improved stent retaining and delivery characteristics. For example, in at least one embodiment wherein the ends of a pant style bifurcated stent are retained about the respective branches of the catheter prior to delivery by one or more socks or sleeves, the distal end of each leg of the stent is retained by a separate sleeve. In some embodiments, the sleeve disposed about the end of the stent leg on the side branch of the catheter engages only a portion of the end of the leg. In some embodiments where the stent is balloon expandable, one or more cones of the balloon are provided with a pleated configuration prior to expansion. The pleated configuration acts to axially lengthen the cone during expansion of the balloon in order to aid in displacing the sleeve disposed about the end of the stent from the end of the stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 2 is a longitudinal side view of the catheter shown in FIG. 1 configured in accordance with an embodiment of the invention.

FIG. 3 is a cross-sectional view of the catheter shown in FIG. 2.

FIG. 4 is a more distal cross-sectional view of the catheter shown in FIGS. 2 and 3.

FIG. 13 is a partial longitudinal side view of the configuration of the catheter shown in FIG. 12 wherein the balloons are shown in the expanded state.

DETAILED DESCRIPTION OF THE INVENTION

Figure 1:
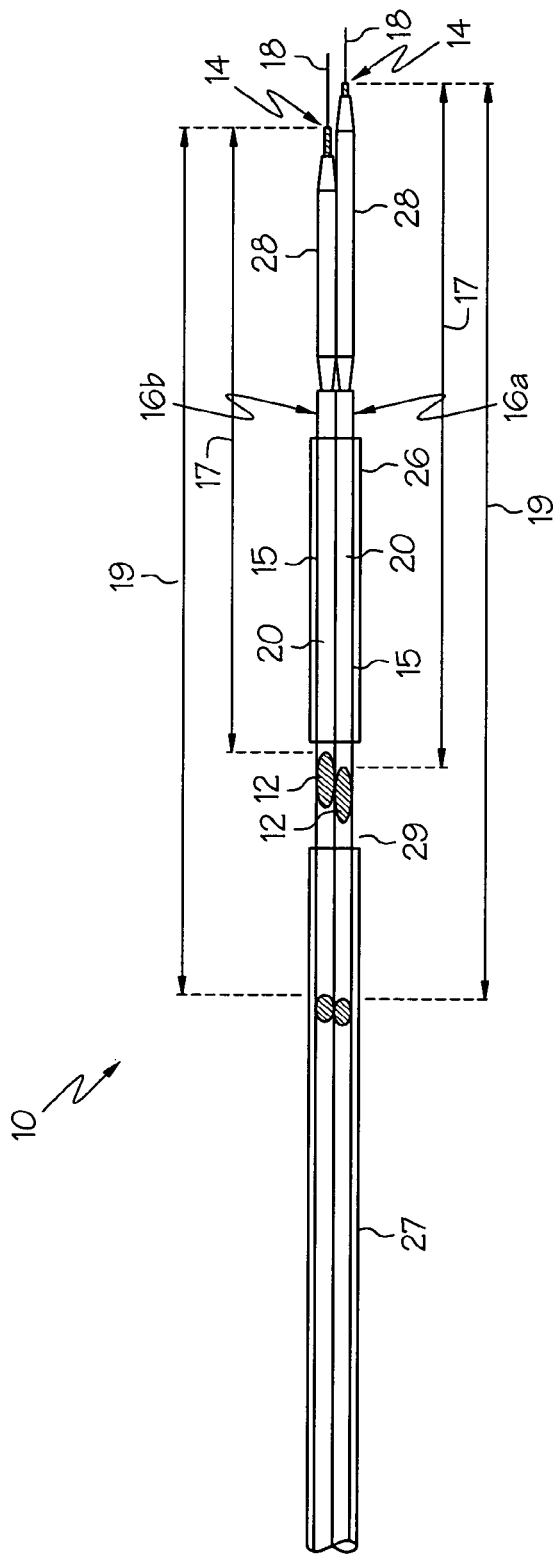
FIG. 1 is a longitudinal side view of a catheter configured in accordance with an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above some embodiments of the present invention are directed to providing a bifurcated catheter with improved radial alignment characteristics in order to provide the side branch or leg of the catheter with greater ease in being positioned adjacent to the opening of the vessel side branch or being advanced therein as the entire catheter is advanced through the main vessel. By improving the radial alignment characteristics of the catheter, other performance characteristics of the catheter may also be improved, such as for example the likelihood of needing to apply excessive amounts of torque or other forces to the catheter in an effort to manipulate the side leg into alignment with the side branch of the vessel will be reduced or eliminated.

The present invention provides a bifurcated catheter with improved radial alignment in a variety of ways. In at least one embodiment, an example of which is depicted in FIG. 1, a catheter 10 is provided with a reduced exchange length. The "exchange length" of the catheter refers to the length of the catheter shaft 20 between the guidewire port 12 and the distal tip 14 of a given branch 16a and 16b of the catheter 10.

In the embodiment shown in FIG. 1 the exchange length, indicated by length 17, of either branch may be about 10 cm to about 20 cm. In at least one embodiment the exchange length is no more than about 15 cm. In many prior catheter designs, often the exchange length is at least 25 cm, such as is illustrated by the length shown at 19. By reducing the exchange length of either or both of the catheter branches 16a and 16b, the branches 16a and 16b will have less mass traveling over the respective guidewires 18 (the shaft 20 or each branch 16a and 16b defines a guidewire lumen 15, the catheter 10 is advanced to a vessel bifurcation along the guidewires 18). Thus, by providing at least the secondary branch 16b with a shorter exchange length 17, the amount of material of the shaft 20 that needs to turn during rotation is reduced, thereby providing the branch or branches with improved torque characteristics. This reduction in the amount of material in frictional engagement with the guidewire 18 allows the branch 16b to rotate with less force than the force that the two wires 18 provide thereby increasing the likelihood of proper radial alignment.

In some embodiments a catheter 10 may additionally or alternatively be provided with a 'twist' or displacement of one branch about the other, such as for example in the embodiment shown in FIGS. 2-4.

In the embodiment shown, the portion of the catheter distal of the guidewire ports 12, i.e. distal portion 22, is twisted so as to displace one branch, such as the secondary branch 16b about the primary branch 16a. The extent of the displacement of the distal portion 22 of the branches 16a and 16b relative to one another may vary. In at least one embodiment however, such as in the example shown in FIGS. 2-4, the maximum displacement of the branch 16b, relative to its nominal position (illustrated in FIG. 3) on the circumference of the primary branch 16a, is about 90 degrees, such as is shown in FIG. 4. It should be noted however, that depending on anatomical and other variables the catheter 10 may be provided as desired with varying degrees of displacement, such as less than about 90 degrees or more than about 90 degrees.

Providing the catheter 10 with a twisted distal portion 22 provides the catheter with additional torque as it is advanced. As a result when the distal portion 22 of the catheter 10 begins to rotate as it is advanced into a vessel bifurcation the additional torque provided by the twisted configuration shown will enhance the catheters tendency or capability to rotate, thereby further enhancing the radial alignment of the catheter 10.

Additionally, in a catheter which has shafts that are normally elliptical in cross-sectional shape, providing such a catheter with a twisted configuration eliminates the axial bias of the two shafts elliptical end shape.

As is shown in FIGS. 1 and 2, often times a catheter 10 is provided with a distal sheath or sleeve 26 between the guidewire ports 12 and the stent delivery area and/or balloon 28. In such embodiments the sheath may aid in retaining the lateral position of the side branch relative to the parent branch as the catheter is advanced.

In some embodiments of the invention the sheath 26 overlaps less than half of the portion of the branches corresponding to the exchange length 17. In at least one embodiment the distal sheath 26 has a distal end that is about ½ inch distal of one or both ports 12. In at least one embodiment the distal sheath 26 has a proximal end that is about 1 inch proximal to the one or more of the balloons 28. Other positions and lengths of the distal sheath 26 may also be provided.

In at least one embodiment the distal sheath 26 may be continuous with the proximal sheath 27 and define a port opening region 29 therein to allow the guidewires 18 to pass therethrough.

Figure 5:
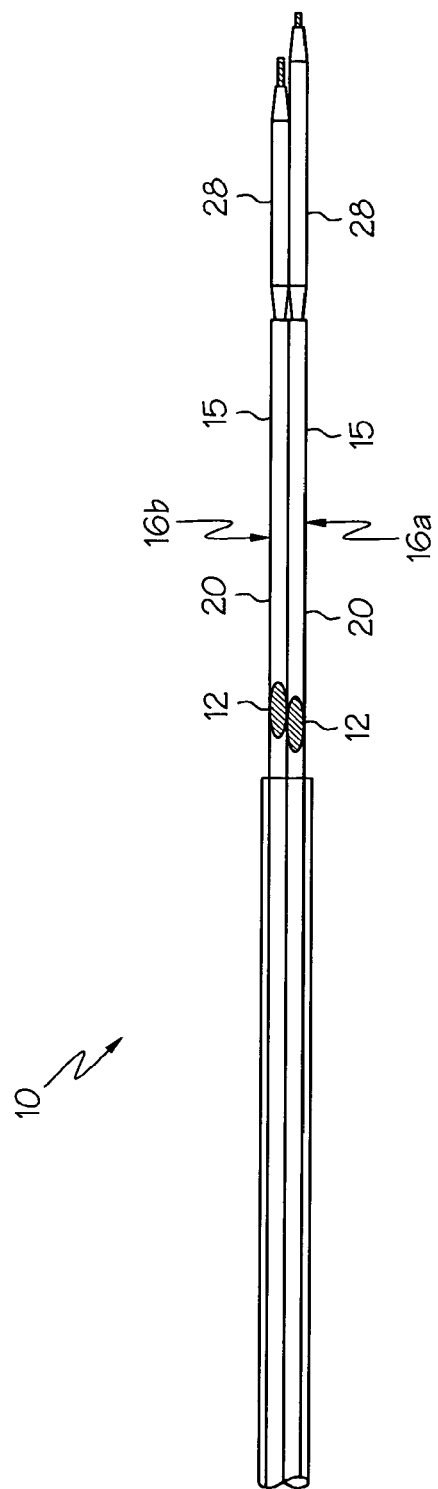
FIG. 5 is a longitudinal side view of the catheter shown in FIG. 1 configured in accordance with an embodiment of the invention.

In some embodiments the sheath is completely removed from the catheter 10, such as in the embodiment shown in FIG. 5. Without the sheath present, the individual branches 16a and 16b are provided with the freedom to move radially with respect to one another. As a result, as the catheter is advanced along the guidewires 18, the branches 16a and 16b more readily rotate into the desired radial alignment at a vessel bifurcation.

In some catheter configurations the side branch 16b will tend to bend rather than provide torque to turn the catheter 10 into position at the vessel bifurcation. If the forces/torque generated by the two wires were not dissipated by bending the side branch 16b, the system would tend to transfer the torque to the catheter to provide better radial alignment. In some embodiments a catheter 10 may additionally or alternatively be provided with a side branch 16b that has a portion of the shaft 20 that has increased stiffness relative to the primary branch 16a. In at least on embodiment, such as in the embodiment shown in FIGS. 6-9, the portion of the shaft 20 underlying a stent retaining region and/or balloon 28 is provided with increased stiffness by disposing a stiffening member or sheath 32 at least partially about the shaft 20. By increasing the stiffness of the 'balloon segment' 34 of the shaft 20, the branch 16b is provided with a greater resistance to bending. As a result, the torque generated by the stiffer segment 34 is transferred to the catheter to aid in radially aligning the catheter as it is advanced into a vessel bifurcation.

Figure 6:
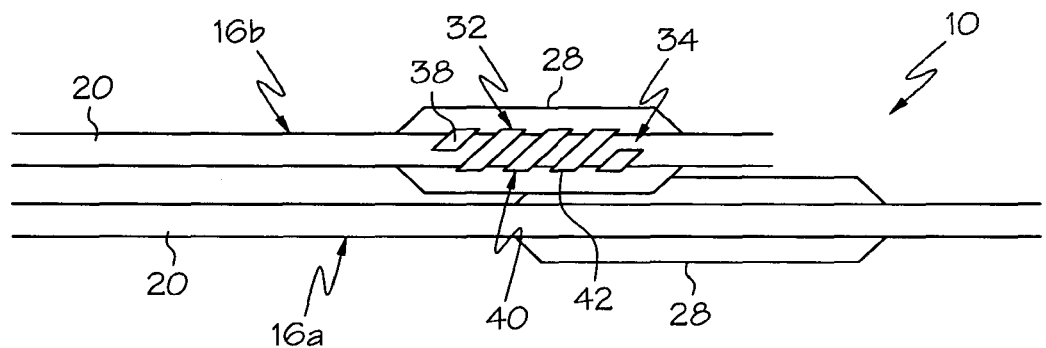
FIG. 6 is a partial longitudinal cross-sectional view of the catheter shown in FIG. 1 configured in accordance with an embodiment of the invention.

In the embodiment shown in FIG. 6, the stiffening member 32 is a spiral strip or ribbon 38 of material such as high density polyethylene (HDPE), poly ether ether ketone (PEEK), nano-composites, stainless steel, polyamide and/or other suitable material or materials, that is wound about the balloon segment 34 of the shaft 20 of the secondary branch 16a. As is shown, the spiral ribbon 38 defines a plurality of spaces 40 between the individual loops or bends 42 of the spiral 38. Such a configuration provides the segment 34 with increased stiffness, via the presence of the ribbon 38 without significantly sacrificing trackability of the catheter 10, as the spaces 40 allow some degree of flexibility despite the increased stiffness.

Figure 7:
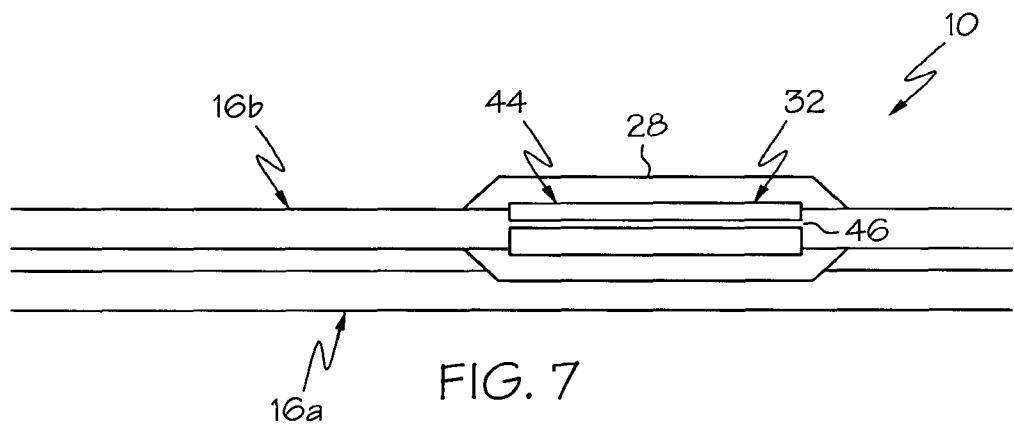
FIG. 7 is a partial longitudinal cross-sectional view of the catheter shown in FIG. 1 configured in accordance with an embodiment of the invention.
Figure 8:
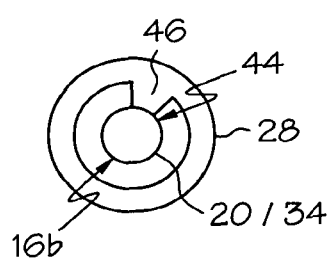
FIG. 8 is a cross-sectional end view of a configuration of the catheter shown in FIG. 7.
Figure 9:
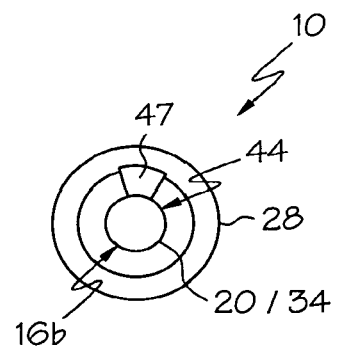
FIG. 9 is a cross-sectional end view of a configuration of the catheter shown in FIG. 7.

Alternatively, in the embodiment shown in FIGS. 7-9, the stiffening member 32 is configured as a tubular member 44 which defines an opening 46 along its entire longitudinal length. Such a 'clam shell' configuration increases stiffness of the segment 34 but allows the branch 16b to more readily bend in one axis for separation of the into the vessel bifurcation. In at least one embodiment, such as in the example shown in FIG. 9, the member 44 may be constructed of HDPE as described above, but rather than simply defining the opening or space 46 free of material as in the embodiments shown in FIG. 8, the space 46 is filled with a stripe 47 of a second, more flexible material, such as low density polyethylene (LDPE), urethanes, Pebax (e.g. 6333 Pebax), and/or other material or materials.

In some embodiments the stiffening member may be substantially tubular in shape but comprise one or more pores, holes, thinned portions, etc, which provides the stiffening member with some degree of enhanced flexibility so that the respective branch retains some ability to bend or flex to an extent desired.

In at least one embodiment of the present invention, such as for example the embodiment depicted in FIGS. 10-13, the catheter 10 is configured to deliver a stent 50, which has a trunk region 52 disposed about a portion of both branches 16a and 16b, and at least one leg region 54. Each leg region 54 extends from the trunk region 52 and is disposed about an individual branch 16a and/or 16b.

The stent 50 may have one or a variety of stent characteristics and may include one or more regions that are balloon expandable, self-expandable and/or hybrid expandable. The stent may be constructed of any of one or more of a variety of stent materials such as stainless steel, shape memory metals including nitinol, polymers, etc.

In many bifurcated stent delivery catheter, the stent retaining portion and/or balloon of the catheter is provided with various configurations of retractable sheaths or members. Prior to delivery, the sheath, often having a split-sheath configuration, is typically disposed about the entire stent and thus confines a significant portion of branches and together. This confinement may reduce the ability of the branches to radially align as the catheter is advanced into the bifurcation.

In order to provide a bifurcated stent delivery catheter 10, such as is depicted in FIGS. 10-13, with improved radial alignment characteristics, the retractable sheath common to many catheters is replaced with a single proximal retractable stent end retaining member or sock 60 and separate retractable distal socks 62. In at least one embodiment, prior to delivery of the stent 50, the proximal sock 60 is disposed about a portion of the trunk region 52 and both branches 16a and 16b. While the proximal sock does overlap both branches 16a and 16b the extent of the overlap is much less that a single sheath extending over the entire stent.

In at least one embodiment the socks 60 and 62 may be self-retracting such that when the stent is made to expand the increasing diameter of the stent causes the socks to roll back, slide or otherwise be retracted from the confines of the socks. In some embodiments, the expanding stent simply pulls out from under the grasp of the sock. In some embodiments one or more of the socks are bio-absorbable.

At the distal end of the stent 50, a portion of each leg region 54 is retained on the respective branch by a separate distal sock 62. In order to facilitate release of an individual leg region 54 without interfering with radial alignment of the catheter 10, a sock 62 may be provided with a variety of configuration to aid in proper retraction and release of the leg region 54. In the various embodiments shown the sock 62 engaged to the end of the leg region 54 of the secondary branch 16b, overlappingly engages less than half of the circumference of the leg region 54.

Figure 10:
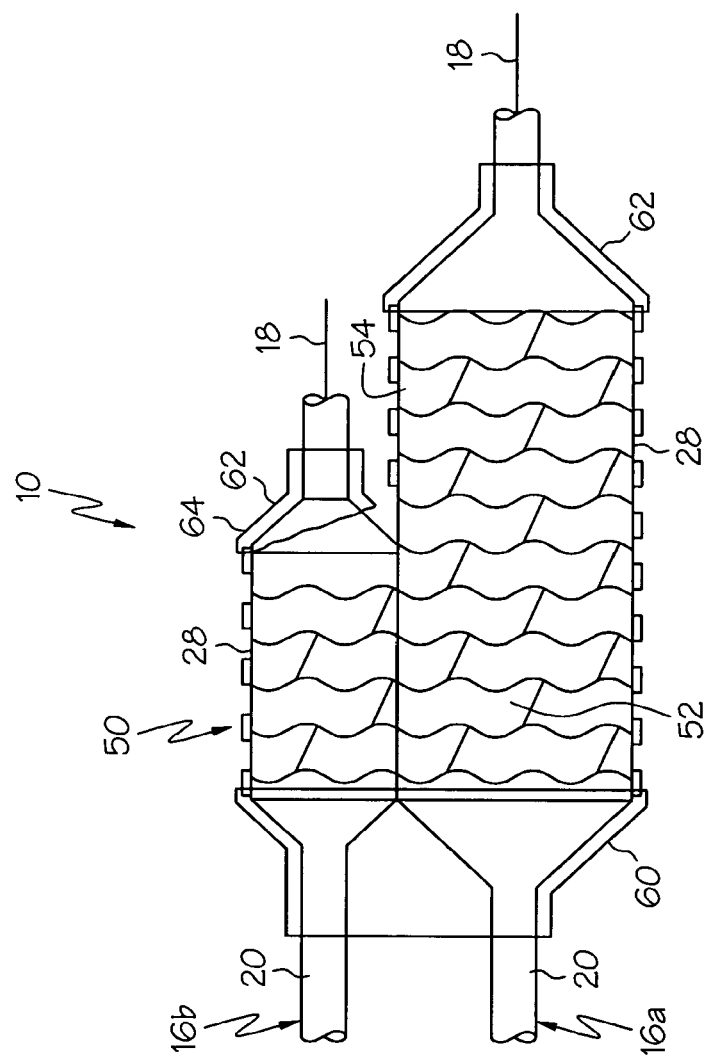
FIG. 10 is a partial longitudinal side view of a catheter configured in accordance with an embodiment of the invention.

For example in the embodiment shown in FIG. 10, one or both of the distal socks 62 may be provided with an angled stent engagement area 64 which partially overlaps a region of the stent 50. The angled stent engagement area 64 allows the sock 62 to be disposed about the end of the trunk region 52 or leg region 54 of a portion of the stent disposed about the secondary branch 16b without interfering with the movement of the primary branch 16a or portions of the stent disposed thereabout. In some embodiments the angled stent engagement area 64 defines an angle relative to the longitudinal axis of the catheter of about 45 degrees or less when disposed about the stent 50.

Figure 11:
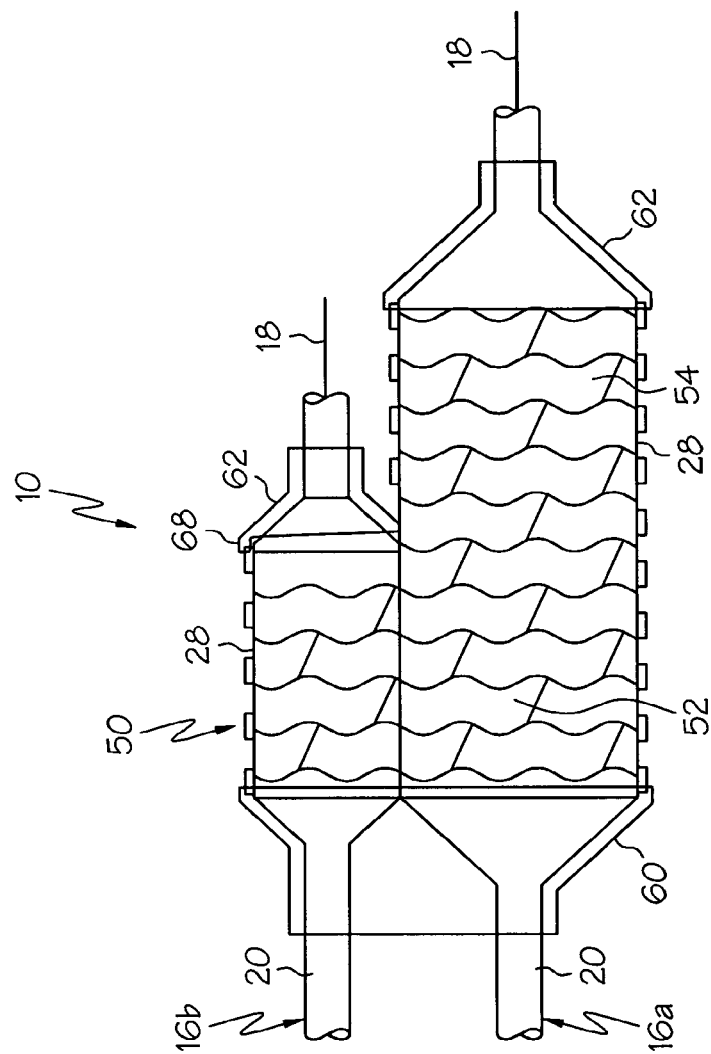
FIG. 11 is a partial longitudinal side view of the catheter shown in FIG. 10 configured in accordance with an embodiment of the invention.

In another example, shown in FIG. 11, one or more of the distal socks 62 may comprise an engagement lip 68 which extends proximally to engage the stent 50 prior to delivery. In at least one embodiment the lip 68 overlaps the stent 50 to a length of about 1.5 mm or less prior to deployment.

Figure 12:
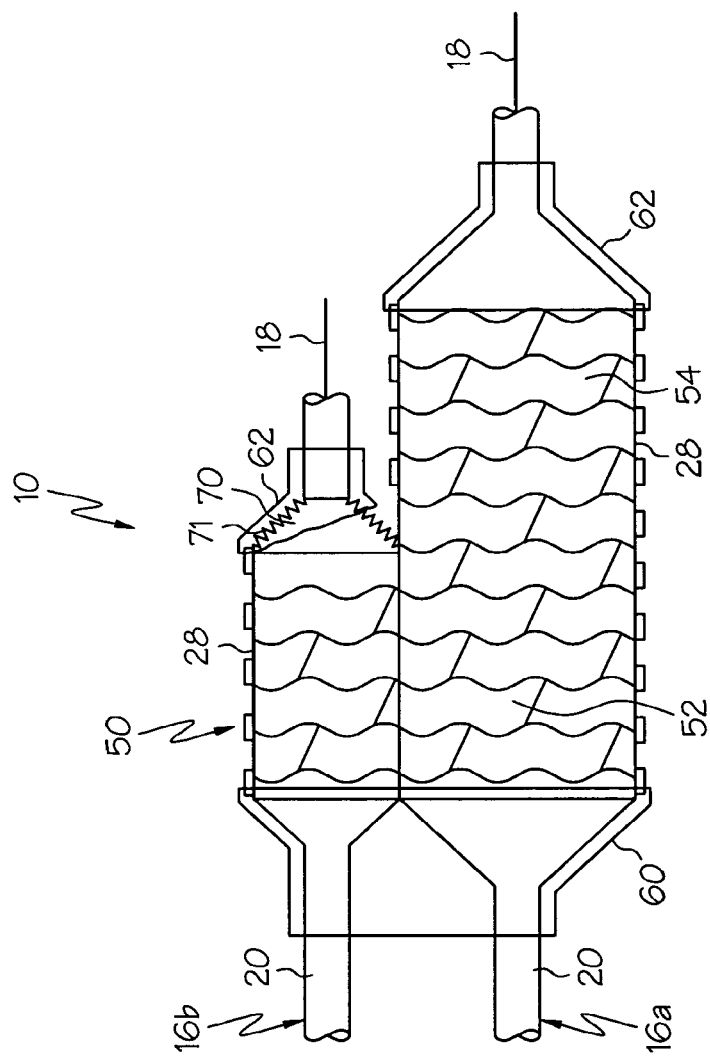
FIG. 12 is a partial longitudinal side view of the catheter shown in FIG. 10 configured in accordance with an embodiment of the invention.

In another example, shown in FIG. 12 the distal socks may have any configuration desired, but the balloon 28 may also have a distal cone 70 which has a pleated configuration in the unexpanded state. When the balloon(s) 28 are expanded to release the stent 50, such as is shown in FIG. 13, the folded pleats 71 unfold, thereby lengthening the cone 70. In some embodiments the length of the cone 70 increases from less than about 0.5 mm to more than 1.5 mm. The lengthening of the cone 70 will tend to displace the distal sock 62 off of the stent 50.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A system for treating a vessel bifurcation comprising:
a bifurcated catheter having a first branch and a second branch, each branch having a proximal region and a distal region, at least a portion of the proximal region of each branch being retained in a first position immediately adjacent one another along a first axis, the first axis extending perpendicular to a longitudinal direction of the catheter, at least a portion of the distal region of each branch being retained in a second position immediately adjacent one another along a second axis, the second axis extending perpendicular to the longitudinal direction of the catheter and being radially displaced from the first axis, the bifurcated catheter maintaining the first and second positions prior to delivery into a vessel, and during delivery through the vessel.

2. The system of claim 1 where in the second axis is radially displaced from the first axis by more than zero degree but less than about 90 degrees.

3. The system of claim 1 where in the second axis is radially displaced from the first axis by more than about 90 degrees.

4. The system of claim 1 where in the second axis is radially displaced from the first axis by about 90 degrees.

5. A system for treating a vessel bifurcation comprising:
a bifurcated catheter having a first catheter branch and a second catheter branch, the bifurcated catheter configured such that the first and second catheter branches are advanced together into the vessel;
the first catheter branch comprising a first catheter shaft having a first proximal end and a first distal end, at least a portion of the first catheter shaft defining a first guidewire lumen and a first guidewire port, the first guidewire port defining a first aperture extending through a sidewall of the first catheter shaft, the first guidewire lumen of the first catheter shaft in fluid communication with the first guidewire port, the first catheter branch having a first exchange length that extends from the first distal end to the first guidewire port, the first exchange length being less than about 20 cm;

the second catheter branch comprising a catheter shaft having a second proximal end and a second distal end, at least a portion of the second catheter shaft defining a second guidewire lumen and a second guidewire port, the second guidewire port defining a second aperture extending through a sidewall of the second catheter shaft, the second guidewire lumen of the second shaft in fluid communication with the second guidewire port, the second catheter branch having a second exchange length that extends from the second distal end to the second guidewire port, the second exchange length being less than about 20 cm; and a sheath, the sheath having a sheath length, the sheath disposed about a portion of both the first catheter shaft and the second catheter shaft distal of the first guidewire port and the second guidewire port, the sheath having a sheath length, the sheath length being less than about half of either the first exchange length and second exchange length.

6. The system of claim 5 wherein at least one of the first exchange length and the second exchange length is less than about 15 cm.

7. The system of claim 5 wherein at least one of the first exchange length and the second exchange length is less than about 10 cm.

8. The system of claim 5 wherein the portion of the catheter corresponding to the first exchange length and the second exchange length is not positioned within a sheath.

* * * * *